United States Patent [19]

Schlager et al.

[11] Patent Number: 4,586,514

[45] Date of Patent: May 6, 1986

[54] PHONOANGIOGRAPHIC SPECTRAL ANALYSING APPARATUS

[75] Inventors: Kenneth J. Schlager, Elm Grove; Jeffrey R. Melvin, Franklin, both of Wis.

[73] Assignee: Biotronics Instruments, Wauwatosa, Wis.

[21] Appl. No.: 521,957

[22] Filed: Aug. 10, 1983

[51] Int. Cl.[4] .............................................. A61B 7/00
[52] U.S. Cl. .................................... 128/773; 128/700
[58] Field of Search ........ 128/773, 700, 711, 660–663, 128/904, 715; 324/77 B

[56] References Cited

U.S. PATENT DOCUMENTS

| | | | |
|---|---|---|---|
| 3,140,710 | 7/1964 | Glassner et al. | 128/700 |
| 3,171,406 | 3/1965 | Baum et al. | 128/715 |
| 4,321,680 | 3/1982 | Bertrand et al. | 324/77 B |
| 4,339,711 | 7/1982 | Inami et al. | 324/77 B |

OTHER PUBLICATIONS

"Evaluation ... by Phonoangiography", Duncan et al., New Eng. J. Med., vol. 293, No. 22, pp. 1124–1128, 1975.

*Primary Examiner*—Edward M. Coven

*Attorney, Agent, or Firm*—Andrus, Sceales, Starke & Sawall

[57] ABSTRACT

A non-invasive clinical instrument provides for in vivo detection of a restriction in an artery. A microphone is applied to the body over the artery and generates a complex electrical signal which is processed to remove noise and amplified. A digital bandpass filter circuit includes a plurality of individual bandpass filters, each of which covers ⅓ of an octave and covers adjacent octaves to cover the complete spectrum between about 2 to 2,000 hertz. Switched-capacitor bandpass filters are used. Each three bandpass filters separated by one-third of an octave are connected such that setting the center bandpass filter automatically resets the two adjacent bandpass filters to cover a single octave in steps of one-third. The sensed signal which is an AC analog signal is transmitted by an analog low pass filter to block undesirably higher frequency components from the digital filters. Digital low-pass filters connect the analog low-pass filter to the bandpass filters. A display unit includes a multiplexor for sequentially transmitting the several bandpass signals to the horizontal input in proper timed relation. Each bandpass filter includes an AC (RMS) to DC (average) converter for establishing an appropriate DC output signal, which is passed through a sample and hold circuit to freeze the display.

13 Claims, 2 Drawing Figures

PHONOANGIOGRAPHIC SPECTRAL ANALYSING APPARATUS

BACKGROUND OF THE INVENTION

The present invention relates to a phonoangiographic spectral analyser apparatus and particularly to such an apparatus for clinical application in non-invasive procedure for the analysis and diagnosis of occluded arteries and the like.

Graphic diagnosis of vascular disorders has historically used invasive procedures such as angiography, or alternatively Dopplet ultrasound anaylsis for a noninvasive procedure.

Analysis of vascular disorder is often critical in the prevention and treatment of vascular diseases such as arterial stenosis, as well as other peripheral vascular deseases. Since early 1970, a non-invasive procedure has been developed by C. F. Dewey, Jr. and R. S. Lees which is identified by the name of phonoangiographic analysis, and the method has been shown to be a basically sound diagnostic procedure for occluded arteries and the like.

Medical diagnosis of the human body has for many years involved the analysis of the heart and interrelated chest sounds generally under the broad identifying name of auscultation. Before the stethoscope, the physician would directly listen to the heart sounds through the chest wall, by placing his ear against the chest wall. Even with the more modern invention of the electronic stethoscopes, various recording instrumentation and the like, such diagnosis remains essentially a qualitative method of diagnosis. Further, development both from the standpoint of the technical instrumentation for processing of the sounds, as well as better knowledge and understanding of sound generation and transmission within the human circulating system is needed for quantitative analysis.

For example, an evaluation of phonoangiography is set forth in an article titled "Evaluation of Carotid Stenosis by Phonoangiography" prepared and submitted by Lees, Dewey et al. in the Nov. 27, 1975 issue of the New England Journal of Medicine. The particular study discussed was directed to carotid stenosis and the author concluded that the method presented was a non-invasive method of bruit analysis which could be used to determine the extent of stenosis. In this procedure, a microphone is applied to an area above the artery. The turbulence associated with a stenosis in the artery produces a bruit (a noise) which is processed by the pick-up device into a spectral display. As noted in the above article, the frequency spectrum provided an appropriate basis for analysis and determination of the location and size of a stenosis. Generally, it has been recognized that the size of the internal diameter of the occluded artery is defined by the equation $$f_o d_o = US = 500$$

where,

U is the blood flow velocity—in millimeters (mm) per second, $f_o$ is the critical frequency of the spectrum in Hertz (Hz), d is the diameter of the arterial opening or passageway in mm, S is equal to 1 (Strouhal) number.

The constant number 500 to which the equation is set is based on estimated flow rate in the artery of 500 mm per second. Appropriate positive measurement experimentation has shown that the formula provides a highly accurate estimate of the occluded diameter of the artery. In particular, the results compare favorably with diagnostic findings based on other established methods such as the Dopper ultrasound method and the digital substractive angiographic method presently in use.

The theoretical work done today has shown a sound basis for use of the process in theory. Prior art work thus included development of and confirming of hemodynamic theories from which one can properly and quite accurately estimate the diameter of the opening in an occluded artery based on the acoustic frequency spectrum, as well as analysis of other diseases and respiration defects which are related to acoustic spectra. Generally, medical usage to date has been related to monitoring the internal carotid artery, but it is recognized that the technique may also be useful in analysing the aortic artery as well as other areas of arterial stenosis. The development of the prior art thus generally involves recording of the measurements and subsequent processing through a digital computer. This of course requires substantial investment and further does not provide an on-line presentation for real time analysis. The computer based instrumentation such as used to-date cannot therefore be considered as a usable concept for use in the small clinic or the doctor's office and the like because of space and cost.

Although the work done to date has clearly established the validity of the diagnostic method as well as the possibility of appropriate accuracy, a significant need remains for a practical clinical instrument. In order to provide a useful clinical instrument, the apparatus must be relatively inexpensive and reasonably portable while maintaining reliability at least equal to present analysis in other forms of instrumentation. Further, it is desirable for clinical analysis to provide a real time instrument with the display of the information in real time and essentially instantaneously with the monitoring of the condition.

In such systems, the measurement is of the audio frequency acoustical signal generated by the human artery as a result of a stenosis condition causing turbulence which is heard as a bruit. Thus, turbulent blood flow produces characteristic sound patterns which will vary in accordance with the size and shape of the occlusion.

SUMMARY OF THE PRESENT INVENTION

The present invention is particularly directed to a non-invasive clinical instrument for in vivo detection of the presence and extent of arterial stenosis and the like. Generally, in accordance with the present invention, the instrument includes means to analyze the frequency spectrum associated with arterial stenosis, and particularly occlusion in the internal carotid artery, in accordance with the equation developed by Strouhal.

Generally in accordance with the present invention, a bruit signal is appropriately processed to raise the signal to a working level and then passed through a digital network for driving an output display which presents the acoustic frequency spectrum of the signal. The information is presented in real time and permits accurate analysis and diagnosis of bruits and the like.

Generally, in a practical embodiment of the present invention, a sound signal microphone is applied to the appropriate portion of the body. The sound signal is suitably processed to remove noise and amplify the signal to a usable level. A digital bandpass filter unit includes a plurality of individual bandpass filters which cover the range of interest and function to analyze and separate the sound into the acoustic frequency spectra. A plurality of switched capacitor bandpass filters provide a convenient and commercially available means of controlling and selecting the frequency spectrum. Thus, a switched capacitor bandpass filter is controlled by applying an appropriate dividing signal to the control input. The AC output signal then being conveniently converted to an appropriate DC signal and coupled through a multiplex system to drive a light matrix arranged to present a visual graphical display of amplitude versus frequency.

In a particularly practical embodiment, the bandpass filter network includes a plurality of integrated circuits, each of which includes three bandpass filters separated from each other by one-third of an octave, such as that manufactured and available from Reticon Corporation, wherein the setting of a center bandpass filter provides automatic appropriate corresponding resetting of the two adjacent bandpass filters to cover a single octave in steps of one-third. The setting of the bandpass filters is conveniently controlled by a clock source/divider for setting of the bandpass filter network units.

The output of the bandpass filter network is a series of signals covering the range of interest. In such a digital filter network, the higher frequency signals should be blocked, or the high frequency components within the signal will generate an alias signal output. The AC sensed signal is therefore preferably appropriately processed before transmission to the digital filters.

The analog signal branch connected to the microphone includes a suitable switch means to open the connection to the microphone for initializing of the system. An overall DC zeroing circuit is connected to the on/off switch to provide for initial calibration of the signal. The microphone signal is impressed on an appropriate level amplifier which produces a useful output signal and cuts off all frequencies above 19 kilohertz (KHz). A switchable low-pass filter is set to pass signals above 1.9 KHz and thus removes the low frequency signals to prevent aliasing at lower spectrum frequencies. The output signal of the analog low-pass filter is therefor an AC signal containing all of the necessary information and consisting of the basic heart beat pulse rate which generates the flow through the artery, with the generated higher frequency bruit signal superposed thereon. The filtered and amplified analog signal is applied to the bandpass filter branch to separate the spectral frequencies in this range. In a preferred embodiment, digital low-pass filters are connected to the analog low-pass filter and further restrict the signal passed to a bank of spectrum separating filters. Each of the latter filters is also a digital filter unit in which the center frequency of the filter is electrically set by a clock signal. A frequency division system provides clocks to all filters.

Each output channel of the bandpass filter network includes an AC (RMS) to DC (average) converter for establishing an appropriate DC output signal. For freezing the display, the signal is passed through a sample and hold circuit the output of which is coupled through an individual gain adjustment to permit appropriate calibration of the signals to the display system.

The display section advantageously includes a suitable multiplexing unit for sequentially transmitting the several bandpass signals to the horizontal row input. A log converter may be introduced into the circuit at this point to provide a DB rather than a linear amplitude scale.

A self-adjusting "Auto-Zero" control is connected to the display circuit to actuate the on/off switch in the analog circuit and to automatically check offset in the several circuits. The "Auto-Zero" control compensates for any offset and thereby adjusts the system to a proper reference. The "Auto-Zero" control may be such as to hold the system stable for a fixed period, after which the operator should again reset the system.

The phonoangiographic instrument of this invention is thus a single, compact integrated clinical device which produces a real-time presentation of a bruit spectrum in a patient. The instrument may be constructed with known technology and hardware and produced at a reasonable cost while producing reliable information to the operator.

BRIEF DESCRIPTION OF THE DRAWINGS

The drawings furnished herewith illustrate the best mode presently contemplated by the inventor and incorporating the several advantages and features heretofore and hereafter set forth.

In the drawings

DESCRIPTION OF THE ILLUSTRATED EMBODIMENT

Figure 1:
FIG. 1 is a pictorial view of an instrument constructed in accordance with the teaching of the present invention.

Referring to the drawings and particularly to FIG. 1, a sound pick-up or sensing unit 1 is shown abutting a human patient 2, and is particularly located adjacent a selected human passage, such as an artery 3. The sensing unit 1 forms a part of a phonoangiographic instrument 4 constituting an embodiment of the present invention. The phonoangiographic instrument 4 is a relatively small, inexpensive clinical instrument which can be readily applied in a small medical institution such as a medical clinic, a physicians offices or the like. Generally, the instrument includes a control unit 5 within which the signal processing circuitry is housed and on which the several controls, such as more fully discussed hereinafter, are provided. The output of the control unit 5 is connected to drive a display unit 6. The instrument processes the sensed signal from the sensing unit 1 and generates a graphical display 7 on the display unit 6 which is directly related to the characteristic of the flow in the artery 3 and which will in particular detect any restriction 8 within the artery. Thus, as previously discussed, a growth or restriction in the artery 3 is generally identified as a stenosis. The output signal of the sensing unit 1 includes a base frequency reflecting the transfer of the blood through the body as a result of the heart pumping action. Superimposed on such pulsed flow signal component is a higher frequency signal related to the size of a stenosis, and of course with its alignment with the sensing unit 1. The size and location of the stenosis 8 can be determined by monitoring and analyzing the several frequencies in the combined complex signal from the sensing unit 1.

In the illustrated embodiment of the invention display unit 6 includes a display screen 9 on which the graphical signal or display 7 is displayed.

Figure 2:
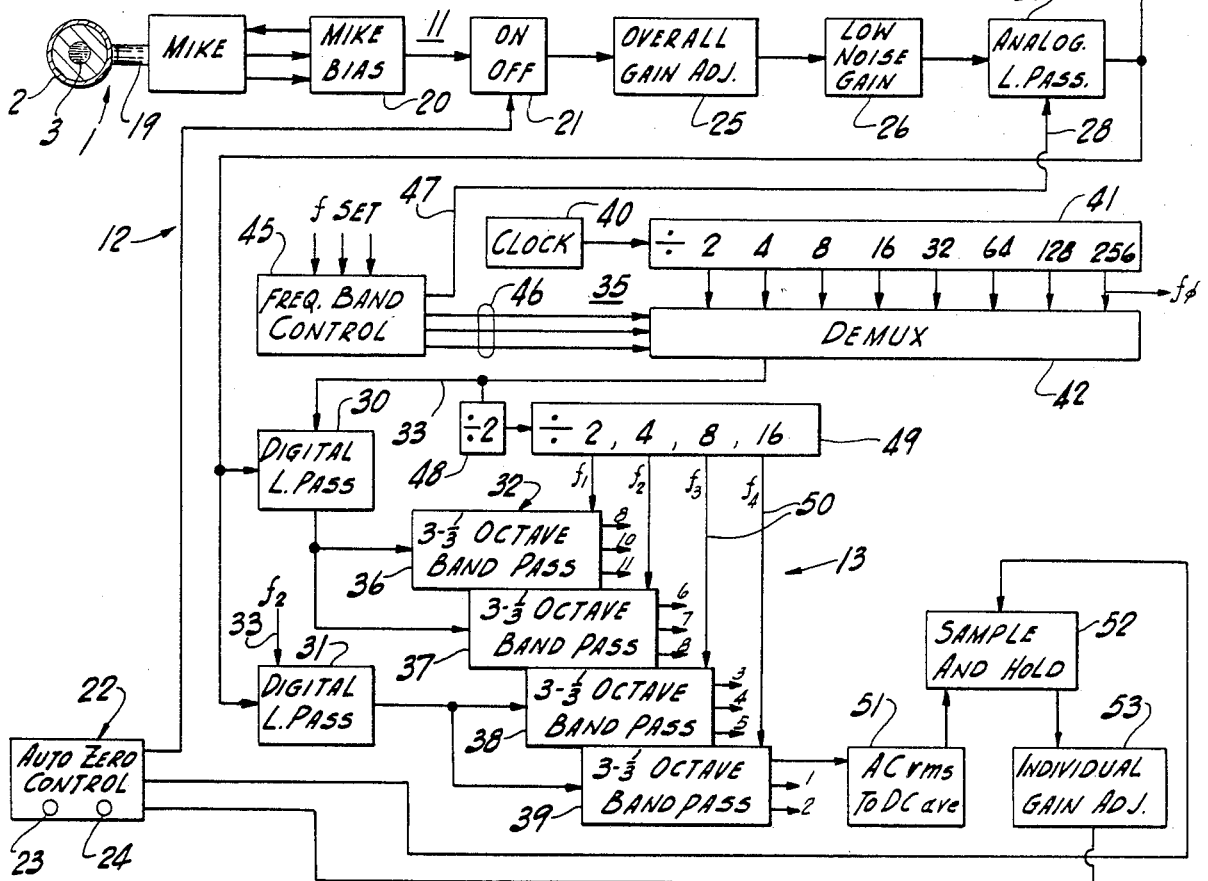
FIG. 2 is a schematic circuit of the instrument.
Figure 2:
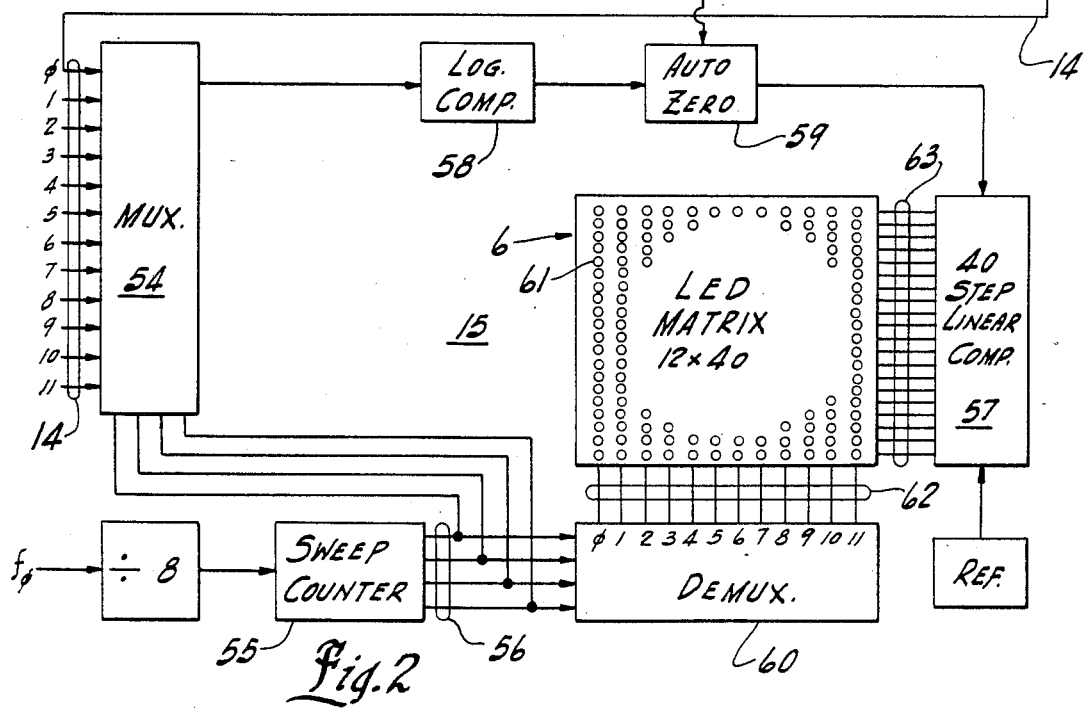

Generally, the signal processing circuitry as shown in the preferred circuit of FIG. 2, includes an analog signal processing branch 11. The sensing unit 1 is connected to the input end of the analog signal branch 11 which produces appropriate filtering and amplification of the signal for subsequent analysis thereof. A digital bandpass filter branch 12 is connected to the output of the analog signal branch 11. The bandpass filter branch 12 includes a digital filter network or means 13 adapted to separate the several frequencies in the complex signal and thus provide a frequency spectrum analysis of the sensed signal. The output of the bandpass filter branch 12 is a multiple line output cable 14, providing an output signal for each frequency of the multiple digital filter means 13. The output cable 14 may include twelve signal lines covering four octaves. A display branch 15 is connected to the cable 14 and to display unit 6. The display unit 6 is driven in synchronism with the generation of the frequency spectrum signals and provides the graphical display 7 of the frequency spectrum in the complex signal. The amplitude of the several signals and the shape of the resulting display is directly related to the frequency characteristics of the bruit. These characteristics are related to the stenosis.

In the present invention, the graphical display 7 is generated in real time so that the doctor or other appropriate observer can analyse information at the same time it is taken, and thereby avoids the necessity of delay and the problems of off-line processing.

In addition, the instrument shown, includes a headphone 17 connected to the output of the analog signal branch 11. A headphone coupling amplifier 18 is connected in circuit to the branch 11 and permits audible monitoring of the signal, simultaneously with the viewing of the graphical display 7.

With this instrument, the doctor or other personnel can directly conduct a thorough and complete analysis of a stenotic condition in an artery or other passage being monitored. The instrument, particularly as more fully developed hereinafter, is constructed of reliable and readily available components, and can be made as a small, compact unit at a reasonable price for use in a small clinic, physician's office or the like.

More particularly, the sensing unit 1 may be any suitable sensitive microphone or other sound pressure responsive device. A particularly satisfactory type is an electret condenser microphone, in which an electret material 2, not shown, having a fixed electric field is mounted in the sound path. When a sound pressure wave strikes the material, a low voltage signal proportional to the sound pressure is created. Such sensing devices are well known and readily available and no further description is given.

The output of the microphone 1 is connected by a suitable cable 19 to the branch 11. A voltage bias unit 20 is connected to place a DC bias signal across an isolation transistor (not shown) which results in creation of the varying low-voltage output signal proportional to the pressure waves. The bias unit 20 passes all frequencies of interest, and the low-voltage signal is processed in branch 11 for driving the subsequent circuitry and the headphones 17.

The signal branch 11 is shown including an on/off control switch 21 connected to the output of unit 20. The on/off switch 21 is employed for initializing the apparatus. An automatic "Auto-Zero" control unit 22 includes a "hold" button 23 and a "reset" button 24. Periodically the operator will activate the reset button which grounds the input signal and effectively initializes the system, which is a condition of no signal input and no display output. Other components in the system which are subsequently described are also connected to the unit 22 for initializing the instrument, and in particular compensating for any offset in the electronic units.

An overall gain adjustment unit 25 is connected to the output of unit 21 and is set to calibrate the signals for proper driving of the display unit 6.

The signal is impressed on an appropriate level amplifier 26 which produces an amplified output signal and cuts off all frequencies above 20 kilohertz (KHz), and thus also functions as a filter. A low-pass filter 27 is connected to the output of filter 26. The low-pass filter 27 is set to pass signals below 1.9 KHZ and thus removes the high frequency signals to prevent aliasing in the digital filters. The filter 27 includes a control line 28, 47 which switches the filter into and out of the signal path.

The output signal of the switchable analog low-pass filter 27 is an AC signal containing all of the necessary information and consisting of the basic heart beat pulse rate which generates the flow through the artery, with the stenosis-generated higher frequency bruit signal superimposed thereon. The analog signal is applied to the bandpass filter branch 12 to separate the spectrum frequencies in this range. The analog signal from branch 11 is also transmitted to the headphone amplifier 18 to provide an audible output of the bruit. The digital filter network or branch 12 is a frequency spectrum filtering system. In a preferred embodiment, first and second digital low-pass filters 30 and 31 are connected to the analog low-pass filter 27 and further restrict the signal passed to a bank of spectrum separating filters 32. Each of the digital filters 30–32, is a switched capacitor filter unit and the center frequency of the filter is electrically settable by an electrical control pulse signal at a central input terminal 33. A standard clock source 35 may provide an adjustable pulse source.

The digital low-pass filters 30 and 31 may be identical units with the input control signal to each at an identical frequency to establish the appropriate signal frequency range transmitted from the analog signal processing branch 11. The filters are advantageously monolithic switched-capacitor bandpass filters such as manufactured and sold under the model number R5620 by Reticon Corporation. As more fully disclosed in the Reticon bulletin 055-0031-18356, the filter is a double-poly, NMOS switched capacitor universal active filter which performs a particular filter function by appropriate connections without the necessity for any external inputs other than an external clock pulse source.

The filter is selected as a low-pass filter by appropriate hardwire circuit connections. The filters 30 and 31 are employed to prevent aliasing in filters 36–39 while filter 26–27 prevent aliasing in filters 30–31.

The bandpass separation filters may consist of four filter IC circuits 36, 37, 38 and 39, each having a series of three filters thereon. Each circuit 36–39 is designed and constructed to cover one octave, and each filter on such circuit covers one-third of an octave. A series of identical circuits will cover a plurality of octaves.

The bandpass frequency spectrum filter may for example be a model RL5604H manufactured and sold by Reticon Corporation. Each chip includes three one-third octave bandpass filters with the singl control input and three one-third octave output leads. Each filter 36–39 is a switched capacitor the same as filter 30 and 31.

The clock unit 35 for setting the digital low-pass filters 30–31, and the bandpass filters 36–39 includes a high frequency clock 40 connected to a multiple output divider 41 to provide a set of frequency ranges. The output of the divider 41 is connected via a demultiplexer unit 42 for transmission of any one of the available programmed divider outputs from the divider 41. A manual frequency set control unit 45 allows the operator to select the frequency and therefore the range.

The control unit 45 establishes a corresponding binary output at three output line 46 to control the demultiplexer unit 42 to select one of the eight available frequency signals. The control unit 45 also has the one output line 47 connected to the line 28 to control the analog low-pass filter 27.

The frequency band control 45 insures simultaneous driving of the analog and digital filters.

The output of unit 42 is a signal of the selected frequency which is simultaneously applied to the input 33 of the digital low-pass filters 30 and 31 and to a divide-by-two divider 48 which is connected to the input of divider 49. The signal applied to the digital low-pass filter 30–31 sets the cutoff frequency and passes the analog signals within the complete range of all four octaves. The output from the unit 42 is also applied to a further four stage divider 49 which provides division by 2, 4, 8, and 16 for connection respectively to the four bandpass filters 36–39, thereby conditioning the bandpass units to cover the four adjacent octaves. The four output lines 50 of the final divider 49 are connected one each to the center filter input of the four bandpass filter units 36–39. As previously noted, this sets the center filter of each circuit to cover the center third of an octave, and the side filters are automatically adjusted through interconnection within the circuit to cover adjacent ranges, and thus each circuit covers one complete octave.

Each output channel line of the bandpass filter network 12 in the embodiment includes an AC-RMS to DC-average converter 51 for establishing an appropriate DC output signal. To give the option of "freezing" the display, the signal is passed through a sample and hold circuit 52, the output of which is coupled through an individual gain adjustment unit 53 to permit appropriate calibration of the signal to the display system 15.

Each one-third octave AC output is thus converted to a DC level corresponding to the average AC level. The sample and hold unit holds the DC level so the operator can remove the microphone without loss of the display. This permits taking a picture of the display. An individual gain adjuster 53 is an internal adjustment to balance all 12 channels.

The output of the filter unit 12 is therefore 12 individual signal lines 14, one for each of the one-third octave with one-third octave center frequency spacing in the four octaves. The four filter circuits thus cover four octaves.

The twelve signal lines 14 from the individual gain adjusters 53 are connected to twelve inputs of a multiplex unit or circuit 54 of the display system 15. A sweep counter 55 having a four-bit binary output 56 is connected as a control to the multiplex unit 54 for sequentially transmitting, in rapid and continuous sequence, the individual signals at the twelve input signal lines to a level comparator 57.

In the illustrated embodiment of the invention, the output of the multiplexer 54 is connected to a logrithmic converter 58, the output of which is operable to convert the amplitude signal to a log function. This provides a display in decibels. A switch means is provided for bypassing of the log unit for transmission of the amplitude signal, if a direct amplitude analysis is desired.

An automatic "zero" circuit 59 is connected to the output of the log comparator and provides a self-zero adjustment as a result of activation of the auto-zero control unit 22, and particularly, pushing the "reset" button 24. The auto-zero circuit cancels any DC level not related to the signal. The output of the auto-zero circuit is connected to the comparator, shown as a forty step linear comparator.

Each one-third octave signal is compared within the forty step linear comparator to give an appropriate amplitude position on the display 6. Each signal is appropriately located on the screen by driving of an LED matrix of the display 6 from a demultiplexer 60. The output of the demultiplexer 60 includes twelve output terminals or lines corresponding to the twelve lines from the filter section 12. The demultiplexer 60 is driven from the sweep counter 55 in synchronism with the drive of the multiplexer 54. Thus, the zero signal line from the bandpass filter branch 12 is transmitted to a corresponding zero reference position on the x-axis of the display.

The LED matric is a cartesian array including twelve columns, each column including forty LEDs 61 which are correspondingly connected to one of the sweep lines 62 from the "demux" unit 60. The forty LEDs of the twelve vertical columns are connected by horizontal drive lines 63 of the forty step linear comparators 7.

A particular LED 61 activation is determined by the simultaneous activation of the corresponding vertical line 62 and the horizontal drive line 63, in accordance with known matrix operations.

All twelve frequency spectrum signals are continuously maintained while the multiplexing system 54, 55, and 60 sequences these signals to the display. The repetitive rate of energizing the lamps 61 is at such a rate that a non-flickering, continuous brightness display is presented and maintained.

In summary, in the illustrated embodiment of the invention, the operator properly positions the patient and places the microphone on the skin directly above the area of interest. The microphone 7 is attached and the instrument turned on. The operator first operates the "reset" button 24 to provide activation of the automatic zero control unit 22 thereby, automatically removing any offset DC signal and setting the system at an appropriate DC zero reference level. After an appropriate period during which the system settles out, the auto zero control restores normal operation thereby activating the apparatus to respond to the signals generated in the microphone 7.

The microphone 7 detects the audio-frequency acoustic signals generated in the artery as a result of the blood flow. The signal consists of the basic frequency signal generated by the heart pressure in combination with a high frequency signal directly related to any turbulence in the blood flow. The turbulent blood flow produces characteristic sounds within the pattern of the signal which is directly related to the size and the shape of the occulsion in the artery. Generally, as previously noted, the acoustical signals of interest fall in a rather narrow frequency spectra, such as 1.2 to 2 thousand hertz.

The signal is processed by the analog signal branch 11 to provide an appropriately filtered and amplified useable signal for electronic analysis. This signal is directly monitored at the headphones 17 in generally the same nature that a doctor is used to listening with a stethoscope.

The bruit signal is also applied to the filter network or branch 12 where the signal is simultaneously applied to all of the bandpass filter units 36–39. The analog low-pass unit 27 and the digital low-pass filters 30–31 prevent passage of the high frequency signals which can adversely affect the operation of the bandpass filter units 36–39. As a result, the complex signal is electronically separated by the bandpass filters into twelve frequency signals within the total range of 2 to 3200 Hz as selected by the operator by adjustment of the frequency band control 45.

The twelve outputs are applied to the display unit 6 where the signal level within each range of each bandpass filter 36–39 is displayed such that the output is a graphical display of the spectral content of the signal in the selected range.

The doctor or other operator can by simultaneously viewing the screen and listening to the sound signal in the headphone provide an extensive diagnosis. Thus, the doctor hears and views the bruit signals essentially in real time; that is, the signals are viewed simultaneously with the creation of such signals. By moving of the microphone 1 on the patient the doctor can more completely and precisely locate and determine the nature of the occluded artery, if any. The instrument by providing a real time output, particularly adapts the unit to clinical application and usage. The instrument can be readily applied to the generally accepted practice of monitoring the internal carotid artery, but may also be applied to the lesser analyzed aortic artery, as well as many other areas of arterial stenosis. In the present invention, both the heart related signal and the stenosis-related signal are transmitted and processed through the circuit. The AC to DC averaging is created over a period of two to five seconds. This of course forms essentially three heart beats. The averaging of the heart beat with the higher frequency signals creates an output signal wherein any change is related to the bruit frequency signal superimposed on the heartbeat signal. This permits the continuous analysis in real time without the processing and delay such as imposed in general by the prior art methods. In the prior art systems the information is recorded for a selected area and then played back with appropriate modification to separate the signals. This is necessary to separate the systolic and diastolic action of the heartbeat on the analysis.

The system as illustrated is a relatively low-cost instrument. For example, such instrument can be readily constructed for marketing at a cost under $5,000.00. This is in contrast to the conventional 30,000 to 40,000 dollars regularly demanded for other forms of vascular detection means.

The operator would normally use a Polaroid camera or the like to sequentially record by appropriate photographs the displays. Although this provides a practical method of implementation for storing the results, an improved result can be obtained by providing a microprocessor-based data storage and reporting system. For example, a simple microprocessor 65 can be coupled to the forty step linear comparator 57 and the output signal coupled to drive the LED matrix 6 may be simultaneously, or alternatively, supplied to the microprocessor 65 and the information stored in the processor memory for subsequent printout or the like. The microprocessor thus serves as a simple recording device, with the analysis and diagnostic treatment provided by the operator simultaneously viewing and listening to the sensed results.

The present invention thus provides a low-cost instrument which establishes on-line and real time analysis of sounds generated within the body as a result of blood related flow and the like. The instrument is readily used in implementation of the several theories relating to the generation and transmission of sounds in the human circulation system, such that a direct diagnosis of the circulation system can be made. Spectral analysis is displayed in a graphical fashion in columns of light emitting diodes, with each column corresponding to the more predictive frequency band. The present invention thus provides a highly significant improvement in practical spectrum analysis normally found and accomplished in phonoangiographic art technology, without the necessity of the time consuming and expensive fast fourier transform functions and the like.

Various modes of carrying out the invention are contemplated as being within the scope of the following claims particularly pointing out and distinctly claiming the subject matter which is regarded as the invention.

I claim:

1. A phonoangiographic diagnostic instrument for the clinical non-invasive analysis of an internal flow passage of a living patient, and said passage adapted to include a restriction and creating a high frequency signal component on the pulse frequency signal in the passage related to the flow of blood in said flow passage and creating a complex pressure signal, comprising a sensing means adapted to be coupled to the patient to sense the flow and the pressure in said flow passage and generating a related complex electrical signal proportional to the pressure in said passage, said electrical signal including a wide spectrum of high frequencies within a known frequency range corresponding to said high frequency component of said pulse frequency signal, a spectrum filter means connected to said sensing means and including a plurality of bandpass filters, each of said filters convering an octave of a plurality of adjacent octaves within said high frequencies of said complex electrical signal to cover the full frequency spectrum related to the flow in the internal flow passage with an obstruction in said passage, conversion means connected to the output of the filter means to average the signal of each individual filter over a plurality of cycles of the pulse frequency related to the flow of blood in said flow passage and establishing a flow regulated electrical output signal, a display means coupled to said conversion means for essentially simultaneously and conjoint on-line display of the said flow related electrical output signals of said bandpass filters and thereby restriction related flow in said passage.

2. The instrument of claim 1 wherein said display means includes a matrix of visual display elements connected to first and second sets of array drive lines, said first set of lines being connected to a timing means and said second set of lines being connected to said filter means, and including sample and hold means to store the output of said filter means, and a common comparator means sequentially coupling said filter means and said second set of drive lines.

3. The instrument of claim 1 including means connected to said filter means to average the output signal over a plurality of heart beat cycles and thereby establish an output signal in which changes accurately represent obstruction in the passage.

4. The diagnostic instrument of claim 1 wherein each of said filter means includes an electrically responsive control means to set the frequency bandwidth of the filter means, and a frequency range selection means connected to said control means.

5. The diagnostic instrument of claim 1 wherein each of said bandpass filters includes an electrically responsive control means to set the frequency bandwidth of the bandpass filter, and a frequency range selection means connected to said control means, an analog filter means connected to said sensing means and a digital pre-filter means connected to said analog filter means, said analog filter means establishing a first upper limit to the frequncy of said transmitted signal and said digital pre-filter means establishing a second upper limit of the frequency of said transmitted signal below said limit of said analog filter means and said spectrum filter means being connected to said digital filter means.

6. The phonoangiographic instrument of claim 3, wherein said digital pre-filter means limits the transmitted signal to a selected maximum frequency.

7. The phonogiographic instrument of claim 1 wherein said bandpass filters includes switch-capacitor filters each having an electrically responsive control input means responsive to a digital control signal, and having an adjustable pulse source means connected to said electrically responsive control input means and including means to change the pulse frequency and thereby control the transmitted frequency range of the several filters.

8. A phonoangiographic diagnostic instrument for clinical non-invasive analysis of an internal flow passage of a living patient, comprising a sensing means adapted to abutt the patient at the passage and generating a complex signal proportional to the sound pressure created by restriction in said passage and including a spectrum of frequencies within a known frequency range correspondening to the high frequencies of said high frequency signal component, a digital bandpass filter unit including a plurality of bandpass filter means, each of said bandpass filter means covering a different range of frequencies and related to the range of other filter means to completely cover the frequencies of a plurality of adjacent octaves and thereby cover the complete frequency spectrum of said high frequencies related to the flow in the passage and substantially within the frequencies between substantially less than 100 hertz and essentially 1,000 hertz, each of said filter means including an electrically responsive control means to set the frequency bandwidth of the filter means, a frequency range selection means connected to said control means, and a display means coupled to said digital bandpass filter unit for simultaneous and conjoint on-line display of the output of all said bandpass filter means and thereby restriction related flow.

9. The phonoangiographic instrument of claim 8 wherein said digital filter is operable to a maximum frequency and having a pre-filter means connected to the digital filter unit, said pre-filter means limiting the transmitted signal to a selected maximum frequency of said filter means.

10. The phonoangiographic instrument of claim 9 wherein said pre-filter means includes an analog filter means connected to said sensing means and a digital filter means connected to said analog filter means and to said digital bandpass filter means, said analog filter means establishing a first limit to the frequency of said transmitted signal and said digital filter means establishing a second upper limit of the frequency of said transmitted signal below said first upper limit.

11. The phonoangiographic instrument of claim 9 wherein said digital filter means include a plurality of integrated circuit filter units, each of said filter units includes a plurality of separate filters of adjacent frequency ranges, each of said circuit filter units having a control input operable to set the frequency range of a first controlled filter of said separate filters and said other filters of the same unit being interconnected to said first controlled filter and a frequency range adjacent the frequency range of said controlled filter.

12. The phonoangiographic instrument of claim 11 wherein each filter unit includes three of said separate filters, one of which is said controlled filter, said controlled filter covering the center frequency range of the filter unit.

13. The phonoangiographic instrument of claim 11 wherein said filter unit is a switch capacitor filter having an electrically responsive control input means responsive to a digital control signal, and having a pulse source means connected to said input means, said source means including means to change the pulse frequency and thereby control the transmitted frequency range of the filter unit.

* * * * *

UNITED STATES PATENT AND TRADEMARK OFFICE
CERTIFICATE OF CORRECTION

PATENT NO. : 4,586,514

DATED : May 6, 1986

INVENTOR(S) : KENNETH J. SCHLAGER ET AL

It is certified that error appears in the above-identified patent and that said Letters Patent is hereby corrected as shown below:

In Column 1, line 14, delete "anaylsis" and substitute therefor --analysis--

In Column 1, line 19, delete "deseases" and substitute therefor --diseases--

In Column 7, line 1, delete "singl" and substitute therefor --single--

In Claim 5, column 11, line 22, before "and said spectrum" insert --,-- (comma)

In Claim 7, column 11, line 27, delete "phonogiographic" and substitute therefor --phonoangiographic--

In Claim 8, column 11, line 39, delete "abutt" and substitute therefor --abut--

In Claim 11, column 12, line 35, after "filter and" insert --set to--

Signed and Sealed this

Sixteenth Day of December, 1986

*Attest:*

DONALD J. QUIGG

*Attesting Officer*    *Commissioner of Patents and Trademarks*